United States Patent [19]
Kimura et al.

[11] Patent Number: 4,623,396
[45] Date of Patent: Nov. 18, 1986

[54] TITANIUM-MICA COMPOSITE MATERIAL

[75] Inventors: Asa Kimura, Tokyo; Fukuji Suzuki, Atsugi, both of Japan

[73] Assignee: Shiseido Company Ltd., Tokyo, Japan

[21] Appl. No.: 648,849

[22] Filed: Sep. 7, 1984

[30] Foreign Application Priority Data

Sep. 14, 1983 [JP] Japan .............................. 58-170345
Feb. 15, 1984 [JP] Japan .............................. 59-26716
Feb. 15, 1984 [JP] Japan .............................. 59-26717

[51] Int. Cl.$^4$ .............................................. C09C 3/06
[52] U.S. Cl. ..................................... 106/291; 106/300
[58] Field of Search ................. 106/300, 291; 428/403

[56] References Cited

U.S. PATENT DOCUMENTS 3,711,308 1/1973 Brand et al. ........................ 106/291
4,537,636 8/1985 Bernhard et al. .................... 106/291

*Primary Examiner*—Amelia B. Yarbrough
*Attorney, Agent, or Firm*—Sprung Horn Kramer & Woods

[57] ABSTRACT

A titanium-mica composite material including (i) mica, (ii) a first coating composed of a titanium compound or a mixture thereof containing titanium dioxide coated on the surface of the mica, and (iii) a second coating composed of titanium dioxide coated on the first coating. The titanium compound in the first coating is at least one compound selected from the group consisting of low oxides of titanium and titanium oxynitrides.

This mica composite material exhibits excellent color tone (e.g., chroma and brightness), good consistency of an appearance color and an interference color, excellent stability, safety, light resistance, acid resistance, alkali resistance, solvent resistance, and heat resistance.

13 Claims, 4 Drawing Figures

TITANIUM-MICA COMPOSITE MATERIAL

BACKGROUND OF THE INVENTION

1. Field of the Invention

The present invention relates to a titanium-mica composite material. More specifically, it relates to a titanium-mica composite material suitable for use as a colorant or pigment providing colored pearl gloss in, for example, cosmetics, paints, printing inks, plastics, ornaments, daily necessities, fiber goods, and ceramics and also suitable for use as a conductive material in, for example, conductive layers and recording layers in recording papers and antistatic materials. The titanium-mica composite material according to the present invention exhibits excellent color tone (e.g., chroma and brightness), good consistency of an appearance color and an interference color, excellent stability, safety, light resistance, acid resistance, alkali resistance, solvent resistance, and heat resistance.

2. Description of the Prior Art

As is well known in the art, conventional titanated mica pigments used in, for example, the cosmetic field comprise very thin mica flake and a titanium dioxide layer formed thereon, as disclosed in Japanese Standard of Cosmetic Ingredient Supplement II, page 54 to 57 (published on 1982 YAKUJINIPPOU SHA. These conventional titanated mica pigments have pearl gloss and various interference colors. These titanated mica pigments are generally prepared as dislosed in Japanese Examined Patent Publication (Kokoku) No. 43-25644 by hydrolyzing an aqueous solution of the inorganic acid salt of titanium (e.g., titanyl sulfate) in the presence of mica to deposit hydrous titanium oxide on the surface of mica, followed by heating, although these titanated mica pigments can also be prepared by a vacuum deposition method. As the starting mica, muscovite is generally used, but biotite or other mica can also be used. The mica is previously subjected to aqueous grinding and sifting to obtain powder particles having a uniform particle size. The resultant titanated mica pigments exhibit various interference colors, depending upon the thickness of the titanium dioxide layer coated on the surface of the mica. The interference colors are generally silver when the titanium dioxide content is 10% to 26% by weight, gold when the titanium dioxide content is 26% to 40% by weight, red, blue, and green when the titanium dioxide content is increased from 40% by weight to 50% by weight, and higher order interference colors when the titanium dioxide content is 50% to 60% by weight. The correlations between the interference color and the thickness of the titanium dioxide layer coated on the surface of the mica are shown in Table 1.

TABLE 1

| Interference color | Geometrical thickness (mµ) of TiO$_2$ |
| --- | --- |
| Silver | 20–40 |
| Pale gold | 40–90 |
| Gold | 40–90 |
| Red | 90–110 |
| Purple | 110–120 |
| Blue | 120–135 |
| Green | 135–155 |
| Second order gold | 155–175 |
| Second order purple | 175–200 |

The conventional titanated mica pigments thus prepared have pearl gloss and various interference colors. However, the appearance colors thereof are always near or close to white and no pigments having bright appearance colors in agreement with the interference colors are obtained.

Various kinds of color pigments such as iron oxides, ferric ferrocyanide, chromium oxides, carbon black, and carmine have been heretofore incorporated into the above-mentioned titanated pigments to obtain various colored appearance. However, the various properties (e.g., stability, safety, light resistance, acid resistance, alkali resistance, solvent resistance, and heat resistance) of these colored titanated mica pigments largely depend upon the properties of the color pigments incorporated thereinto. For example, blue titanated mica pigments containing ferric ferrocyanide result in undesirable color fading in an alkaline solution. Red titanated mica pigments containing carmine result in color fading and deterioration against light. Furthermore, black titanated mica pigments containing carbon black and green titanated mica pigments containing chromium oxides have possible disadvantages from the safety point of view since the carbon black may include carcinogenic 3,4-benzpyrene as an impurity and $Cr^{6+}$ has oral toxicity. Furthermore, the colored titanated mica pigments containing the color pigments cause color segregation or foreign odor generation in a solvent or various compositions (e.g., cosmetics) since the color pigments are incorporated.

The present inventor previously found that colored titanated mica pigments having bright color tone and pearl gloss and excellent safety, stability, light resistance, acid resistance, alkali resistance, solvent resistance, and heat resistance, which are equivalent to or superior to those of the above-mentioned titanated mica pigments or colored titanated mica pigments can be obtained by coating the surface of mica powder particles with a low oxide of titanium or a mixture of titanium dioxide and a low oxide of titanium (see Japanese Unexamined Patent Publication (Kokai) No. 59-126468.

SUMMARY OF THE INVENTION

Accordingly, an object of the present invention is to eliminate the above-mentioned disadvantages in the prior arts and to provide a titanium-mica composite material having an extremely improved color tone (e.g., chroma and brightness), good consistency of the appearance color and the interference color, and excellent pigment characteristics such as stability, safety, light resistance, acid resistance, alkali resistance, solvent resistance, and heat resistance.

Another object of the present invention is to provide a titanium-mica composite material capable of being formulated into cosmetic compositions with good dispersibility and without causing undesirable color fading, color segregation, and foreign odor generation after the formulation.

Other objects and advantages of the present invention will be apparent from the description set forth hereinbelow.

In accordance with the present invention, there is provided a titanium-mica composite material comprising (i) mica, (ii) a first coating composed of a titanium compound or a mixture thereof containing titanium dioxide coated on the surface of the mica, and (iii) a second coating composed of titanium dioxide coated on the first coating. The titanium compound in the first coating is low oxides of titanium and/or titanium oxynitrides.

BRIEF DESCRIPTION OF THE DRAWING

The present invention will be better understood from the description set forth below with reference to the drawings in which.

DESCRIPTION OF THE PREFERRED EMBODIMENTS

Figure 1:
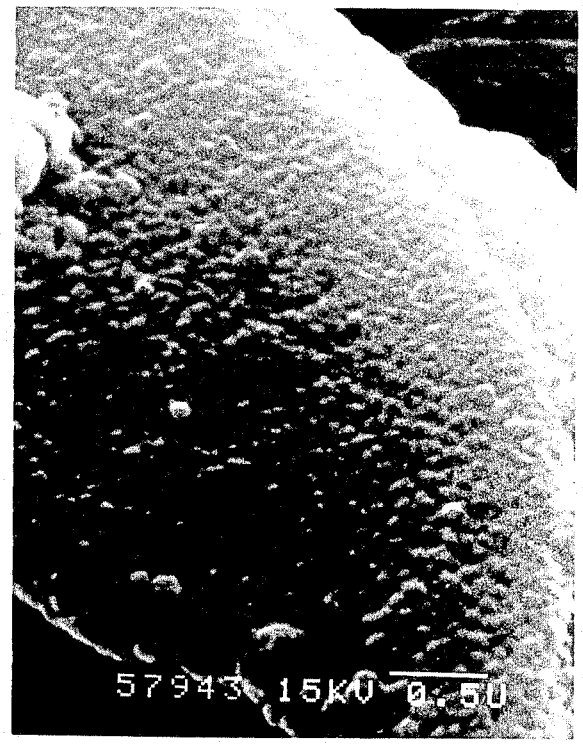
FIG. 1 is a photomicrograph (×30,000) illustrating a metallurgical structure of the particle surface of the intermediate "A" obtained in Example 1.

The mica usable in the present invention is any conventional mica such as commercially available muscovite. However, biotite can also be optionally used. The particle size of the mica may vary over a wide range. However, when the present mica composite material is intended to be used as a coloring agent in a cosmetic composition, mica having a smaller particle size and having a flat shape among the conventionally commercially available mica having a particle size of approximately 1 to 50 μm is preferably used, because beautiful color tone and pearl gloss can be readily obtained.

The "low oxides of titanium" used herein means titanium oxides in which the oxidation degree of the titanium is less than that of titanium dioxide ($TiO_2$). The low oxides of titanium can be represented by the general formula:

$Ti_nO_{2n-1}$ wherein n is an integer of 1 to 100. Typical examples of such compounds are $TiO_2$, $TiO$, $Ti_2O_3$, $Ti_3O_5$, and $Ti_4O_7$. These compounds can be used alone or in any mixture thereof.

The "titanium oxynitrides" used herein means the titanium compounds having the general formula

$Ti_xN_yO_z$ wherein x is 0.2 to 0.6, y is 0.05 to 0.6, and z is 0.1 to 0.9, which comprises a solid solution of nitrogen in titanium monoxide. The values x, y, and z depend upon the amount of the solid-solubilized nitrogen. These compounds can be used alone or in any mixture thereof.

The titanium compound mixtures containing the low oxides of titanium and/or titanium oxynitrides used in the present invention are mixtures of the above-mentioned low oxides of titanium and/or titanium oxynitrides with any other titanium compounds such as titanium dioxide and titanium nitride.

According to the present invention, the mica is covered with the above-mentioned low oxides of titanium and/or titanium oxynitrides or the mixture thereof containing titanium dioxide to form "the intermediate product" according to the present invention. The amount of the above-specified low oxides of titanium and/or titanium oxynitrides in the present intermediate product is preferably 0.01 to 60 parts by weight, more preferably 1 to 40 parts by weight, based on 100 parts by weight of the mica. When the amount of the low oxides of titanium and/or titanium oxynitrides is less than 0.01 part by weight, the colored appearance of the final composite material according to the present invention tends to be not in agreement with the interference color thereof. Contrary to this, when the amount of the low oxides of titanium and/or titanium oxynitrides is more than 60 parts by weight, undesirable agglomeration of the particles tends to occur. Although the thickness of the first coating deposited on the surface of the mica may vary over a wide range, the thickness of the total titanium compounds on the surface of the mica is preferably 200 Å or more, more preferably 900 Å or more, particularly when a composite material having an excellent appearance and interference color other than black is desired.

Although there is no specific limitation in the coating amount of the second coating composed of titanium dioxide in the present composite material, the thickness of the second titanium dioxide coating is preferably 50 Å to 5000 Å, more preferably 300 Å to 2000 Å. When the thickness of the second coating is less than 50 Å, a desired composite material having an excellent color tone usually cannot be prepared. The color tone, especially the consistency of the appearance color and the interference color, becomes better as the thickness of the second coating increases. However, there is no substantial change after the thickness of the second coating becomes 5000 Å.

The titanium-mica composite material according to the present invention can be prepared by various methods, as explained hereinbelow.

The intermediate product according to the present invention (i.e., the mica coated with the first coating composed of the above-specified titanium compounds or the mixture thereof) can be prepared by coating mica with titanium dioxide, followed by heating the resultant titanium dioxide coated mica (or any commercially available titanium dioxide coated mica) in the presence of one or more of reducing gases such as hydrogen and gaseous ammonia or the mixture of these reducing gases with inert gases such as helium, argon, and nitrogen at a temperature of 500° C. to 1000° C., preferably 700° C. to 900° C., to effect the reduction. Thus, the titanium dioxide layer coated on the surface of the mica is mainly reduced to the low oxides of titanium when hydrogen or the mixture of hydrogen with inert gases as a reducing gas is used and the titanium dioxide layer is mainly reduced the titanium oxynitrides when gaseous ammonia or the mixture of gaseous ammonia with inert gases as a reducing gas is used. Alternatively, the commercially available titanium dioxide coated mica (or previously prepared titanium dioxide coated mica) is first mixed with metallic titanium and the mixture is heated, in vacuo, at a temperature of 500° C. to 1000° C., preferably 700° C. to 900° C. Thus, the mica coated with the low oxides of titanium or a mixture thereof is prepared. Furthermore, as disclosed in the above-mentioned Japanese Examined Patent Publication No. 43-25644, an aqueous solution of an inorganic salt of titanium (e.g., titanyl sulfate) is hydrolyzed in the presence of mica powder particles to deposit hydrous titanium dioxide on the surface of the mica powder particles, followed by heating the resultant hydrolyzed product in the presence of the above-mentioned reducing gas or the mixture thereof with the inert gas at a temperature of 500° C. to 1000° C., preferably 700° C. to 900° C., to effect the reduction. Alternatively, the hydrolyzed product obtained above is heated at a temperature of 60° C. to 100° C. to form titanated mica, followed by reducing the resultant titanated mica in the same manner as in the above-mentioned reduction of the commercially available titanated mica pigment. The above-mentioned reduction can be carried out by, in addition to the above-mentioned methods, any other conventional reducing methods. Examples of such methods are such that the above-mentioned titanium dioxide coated mica is reduced by a reducing flame such as hydrogen and that mica is suspended in a titanium salt solution such as a titanium tetrachloride solution, followed by oxidative destruction in a mixed gas flame of air and hydrogen.

The coating of the surface of the intermediate product as prepared above with titanium dioxide can be carried out as follows. That is, the intermediate product comprising the mica coated with the above-mentioned titanium compounds (i.e., the low oxides of titanium and/or titanium oxynitrides) or the mixtures containing the same can be coated with titanium dioxide by heating the same at a temperature of, for example, 140° C. to 400° C. in the air in such a manner that the outerside portion of the previously coated titanium compound layer is oxidized to form the second coating of the present mica composite material. Alternatively, an aqueous solution of an inorganic salt of titanium (e.g., titanyl sulfate) is hydrolyzed in the presence of the above-mentioned intermediate product of the present invention to deposit a hydrous titanium oxide coating on the surface of the intermediate product of the present invention, followed by heating in the air. Furthermore, the above-mentioned intermediate product of the present invention is mixed with metallic titanium, followed by heating in the air to form the desired second coating. These methods can be used together, if desired.

It is essentially important in the titanium-mica composite material according to the present invention that the first coating composed of the above-mentioned titanium compound or the mixture containing the same must be present as an intermediate coating between the innermost mica and the outermost titanium dioxide coating. If this intermediate (or the first) coating is not present, a desired composite material having an excellent color tone such as chroma and brightness and good consistency of the appearance color and the interference color cannot be attained. When the first coating consists of one or more of the low oxides of titanium and titanium oxynitrides, both the appearance color and interference color of the resultant composite material according to the present invention are black. These colors can be changed to various colors such as gold, red, blue, and green by adjusting the amount of the titanium dioxide in the second (i.e., outermost) coating of the present composite material when titanium dioxide is also contained in the first coating together with the low oxides of titanium and/or titanium oxynitrides.

The titanium-mica composite material according to the present invention exhibits excellent color tone (e.g., chroma and brightness), good consistency of appearance color and interference color, excellent stability, safety, light resistance, acid resistance, alkali resistance, solvent resistance, and heat resistance. Accordingly, the present composite material can be advantageously used as a coloring agent or colored pearl gloss-providing agent in various field, including cosmetics, paints, daily necessities, and ornaments.

When the titanium-mica composite material according to the present invention is used in a cosmetic composition, the present composite material can be incorporated into the cosmetic composition in any amount usually used for a coloring agent, pigment, or powder, for example, in an amount of 0.5% to 80% by weight, preferably 5% to 60% by weight. When the amount of the present composite material is too large, the moldability of the cosmetic compound tends to become poor when it is incorporated into solid powder cosmetics. Contrary to this, when the amount of the present composite material is too small, the desired coloring or pearl gloss providing effect tends not to be exhibited.

The present composite material can be incorporated into any conventional cosmetic composition in the form of, for example, liquid creams, lotions, creams, ointments, sticks, powders, pressed powders and multi-layers (e.g., powder-water-oil layers). The present composite materials can be incorporated into various type cosmetics such as facial preparations, make-up preparations, hair preparations, body preparations, and fragrant preparations, preferably make-up preparations such as foundations, rouges, face powders, eye make-ups, lipsticks, and nail enamels.

The other ingredients incorporated into the cosmetic compositions containing the present composite material can be any ingredients which are used in conventional cosmetic compositions. Examples of such ingredients are oils such as higher aliphatic alcohols, higher fatty acids, ester oils, paraffin oils, and waxes; alcohols such as ethyl alcohol, propylene glycol, sorbitol, and glucose; humectants such as mucopolysaccharides, collagenes, PCA salts, and lactates; various surfactants such as nonionic, cationic, anionic, and amphoteric surfactants; thickener such as gum arabic, xanthan gum, polyvinyl pyrrolidone, ethyl cellulose, carboxymethyl cellulose, carboxyvinyl polymer, and modified or unmodified clay minerals; solvents such as ethyl acetate, acetone, and toluene; organic and inorganic pigments and dyes; anti-oxidants such as BHT and tocopherol; water; chemicals; UV absorbers; pH buffers; chelating agents; preservatives; and perfumes.

When the present composite material having bright appearance color in agreement with the interference color is incorporated into cosmetic compositions, the following advantageous effects can be obtained.

(1) Cosmetic compositions having pearl gloss, which exhibit the same color as the appearance color thereof when applied to the skin, can be obtained;

(2) Cosmetic compositions having excellent safety can be obtained;

(3) Cosmetic compositions having excellent long-term stability without causing color fading, discoloration, and foreign odor generation can be obtained; and (4) Cosmetic compositions having excellent dispersion stability without causing color segregation and color shading can be obtained:

EXAMPLES

The present invention will now be further illustrated by, but is by no means limited to, the following Examples, wherein "parts" and "percent" are all on a weight basis unless otherwise specified.

EXAMPLE 1

(Preparation)

A 50 g amount of mica was added to 500 g of ion-exchanged water and was then uniformly dispersed therein while thoroughly stirring. Then, 208.5 g of a 40% aqueous titanyl sulfate solution was added to the dispersion obtained above. The mixture was boiled upon heating for 6 hours while stirring. After cooling, the mixture was filtered and washed with water, followed by calcining (or heating) at a temperature of 900° C. Thus, 80 g of the titanated mica, i.e., the mica coated with titanium dioxide was obtained.

The resultant titanated mica was subjected to a reducing treatment, under a gaseous ammonia stream having a flow rate of 3 liter/min, at a temperature of 700° C. for 6 hours. After cooling, 78 g of the powder particles (i.e., the intermediate "A") exhibiting blue pearl gloss both in the appearance color and the interference color was recovered.

The metallurgical structure of the particle surface of the intermediate "A" is as shown in FIG. 1, i.e., the photomicrograph ($\times 30,000$) obtained by using a scanning type electron micrograph. As is clearly observed from FIG. 1, the surface of the particle of the intermediate "A" was sufficiently coated with the finely divided particles.

Figure 2:
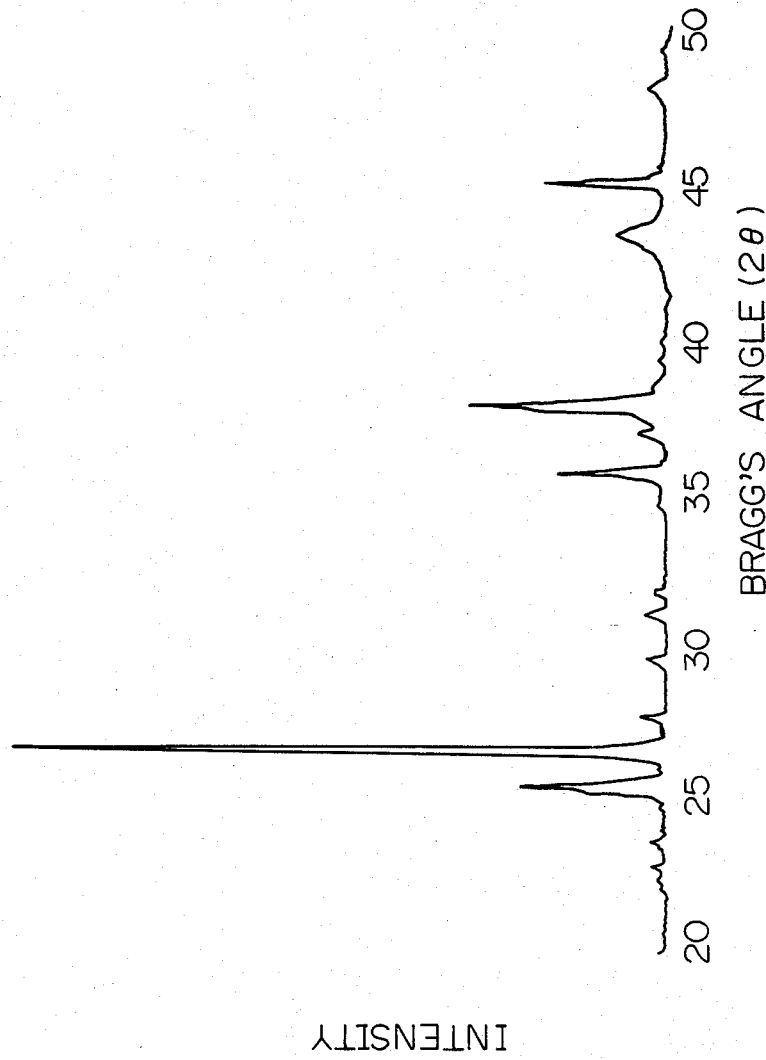
FIG. 2 is a X-ray diffraction pattern chart (Cu-Kα line) of the above-mentioned intermediate "A"

The X-ray diffraction pattern (Cu-K$\alpha$ line) of the resultant intermediate "A" was as shown in FIG. 2. As is clearly observed in FIG. 2, a peak at a diffraction angle (i.e., Bragg's angle $2\theta$) of approximately 25.3° is present in addition to the diffraction peaks of the mica. This peak corresponds to (101) of the strongest peak of the anatase type titanium dioxide. Furthermore, although somewhat broad peaks are observed at the Bregg's angles of approximately 43° and 37° in FIG. 2, these peaks are approximate intermediate points between titanium monoxide (TiO) corresponding to ASTM No. 8-117 and titanium nitride (TiN) corresponding to ASTM No. 6-0642 according to an ASTM examination method. This crystallographically means that the diffraction angles of the titanium oxide and titanium nitride are different because their lattice constants are different, although both compounds belong to the same cubic crystal system. That is, the compound contained in the intermediate "A" having the X-ray diffraction angles $2\theta$ of approximately 43° and 37° is a solid solution of the titanium oxide and the titanium nitride, which is represented by $Ti_xN_yO_z$ as defined above. The composition ratios of mica: titanium dioxide; titanium oxynitride, determined from the ratios of the intensity of the X-ray diffraction were 60%:22.7%:17.3%. Furthermore, the oxygen and nitrogen contents in the intermediate "A" were quantitatively analyzed by means of a model TC-136 gas analyzer (manufactured by LACO Co.). As a result, the oxygen content was 41.7% and the nitrogen content was 4.3%. From the above-mentioned composition analysis data, the resultant titanium oxynitride is represented by $Ti_{0.30}N_{0.19}O_{0.51}$. Thus, it is clear that the intermediate "A" was coated on the surface thereof with the titanium dioxide and titanium oxynitride.

A 50 g amount of the intermediate "A" obtained above was added to 500 g of ion-exchanged water and was uniformly dispersed therein while thoroughly stirring. Then, 300 g of a 40% aqueous titanyl sulfate solution was added to the dispersion obtained above. The mixture was boiled upon heating for 6 hours while stirring. After cooling, the mixture was filtered, washed with water, and dried at a temperature of 200° C. Thus, 100 g of the desired mica coated with titanium compounds in the form of powder particles was obtained. The powder particles thus obtained had an appearance color of bright green and a consistent interference color and exhibited pearl gloss.

Figure 3:
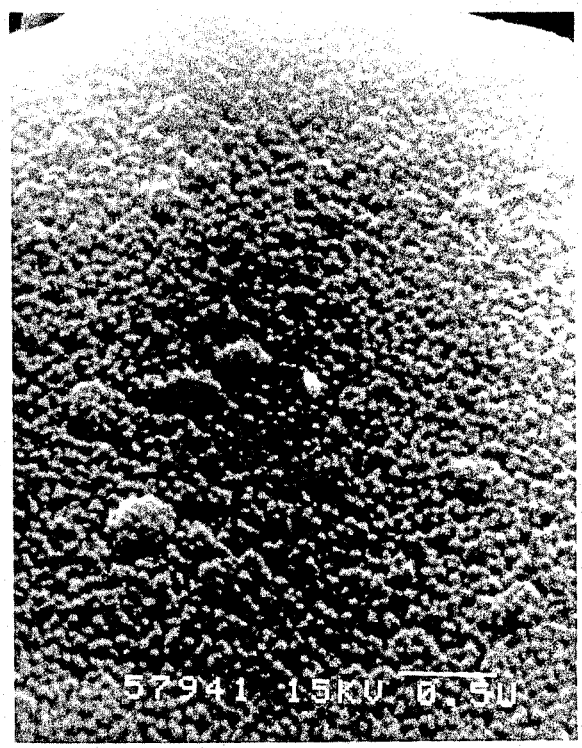
FIG. 3 is a photomicrograph (×30,000) illustrating a metallurgical structure of the product according to the present invention.

The composition of the resultant powder particles thus obtained was 30.3% of mica, 61.0% of titanium dioxide, and 8.7% of titanium oxynitride, as determined by the above-mentioned LACO gas analyzer. The metallurgical structure of the particle surface of the resultant product is as shown in FIG. 3, which is a photomicrograph ($\times 30,000$) obtained by using a scanning type electron micrograph. As is clearly observed from FIG. 3, the surface of the particle of the product was sufficiently coated with the finely divided powder particles.

Figure 4:
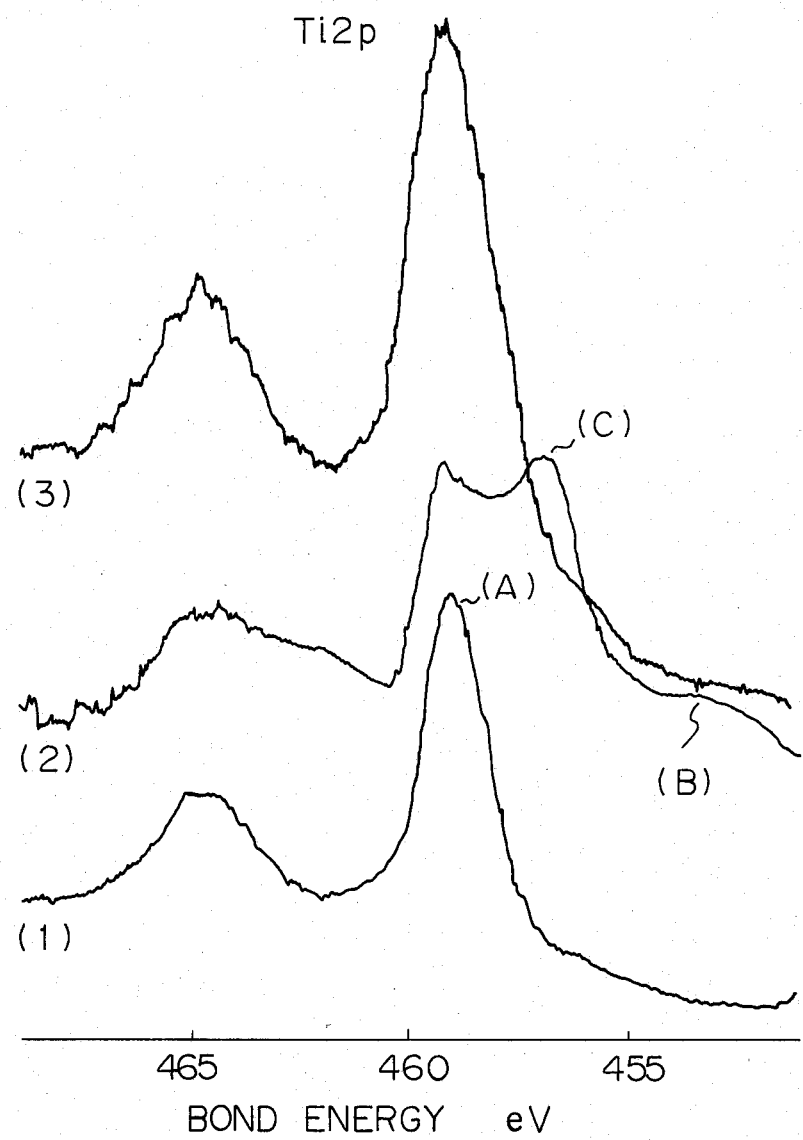
FIG. 4 is an electron spectroscopy of chemical analysis (ESCA) of Ti 2p of the product according to the present invention.

Furthermore, the results of the Ti 2p bonding energy analysis of the resultant product obtained by means of an ESCA are shown in FIG. 4. The apparatus used was ESCA model 650B (manufactured by SHIMADZU CORPORATION). In FIG. 4, a curve (1) was obtained by analyzing the surface layer of the resultant powder particle, a curve (2) was obtained by analyzing a layer, which is located at a 700 Å depth from the surface, of the resultant powder particle, and a curve (3) was obtained by analyzing a layer, which is located at a 1000 Å depth from the surface, of the resultant powder particle. A peak (A) commonly appearing in the curves (1), (2), and (3) is the bonding energy peak of titanium dioxide (Ti-$O_2$), and peaks (B) and (C) only appearing in the curve (2) are the bonding energy peaks of titanium monoxide (Ti-DSO) and titanium oxynitride (Ti-N).

As is clear from the results in FIG. 4, the resultant product in the form of powder particles is composed of the mica coated with the first coating of titanium dioxide and titanium oxynitride and the second coating of titanium dioxide.

EXAMPLE 2

(Preparation)

A 50 g amount of the intermediate "A" obtained in the same manner as in Example 1 was added to 500 g of ion-exchanged water and was uniformly dispersed therein while thoroughly stirring. Then, 200 g of a 40% aqueous titanyl sulfate solution was added to the dispersion obtained above. The mixture was boiled upon heating for 6 hours, while stirring. After cooling, the mixture was filtered, washed with water, and dried at a temperature of 200° C. Thus, 80 g of the desired titanium-mica composite material (i.e., the mica coated with the titanium compounds) in the form of powder particles was obtained.

The resultant powder particle had a bright reddish purple appearance color and a consistent interference color and also exhibited pearl gloss. The compositions of the product determined in the same manner as in Example 1 were 36.6% of mica, 52.9% of titanium dioxide, and 10.5% of titanium oxynitride. It was also observed by a scanning type electron micrograph that the surface of the particle of the product having the reddish purple appearance and interference colors and providing pearl gloss was sufficiently coated with finely divided particles.

EXAMPLE 3

(Preparation)

A 50 g amount of the intermediate "A" obtained in the same manner as in Example 1 was added to 500 g of ion-exchanged water and was uniformly dispersed therein while thoroughly stirring. Then, 250 g of a 40% aqueous titanyl sulfate solution was added to the dispersion obtained above. The mixture was boiled upon heating for 6 hours, while stirring. After cooling, the mixture was filtered, washed with water, and dried at a temperature of 200° C. Thus, 90 g of the desired titanium-mica composite material (i.e., the mica coated with the titanium compounds) in the form of powder particles was obtained.

The resultant powder particle had a bright blue appearance color and a consistent interference color and also exhibited pearl gloss. The compositions of the product determined in the same manner as in Example 1 were 33.1% of mica, 57.4% of titanium dioxide, and 9.5% of titanium oxynitride. It was also observed by a scanning type electron micrograph that the surface of the particle of the product was sufficiently coated with finely divided particles.

EXAMPLE 4

(Preparation)

A 50 g amount of mica was added to 500 g of ion-exchanged water and was uniformly dispersed therein while thoroughly stirring. Thus, 312.5 g of a 40% aqueous titanyl sulfate solution was added to the dispersion obtained above. The mixture was boiled upon heating for 6 hours, while stirring. After cooling, the mixture was filtered, washed with water, and calcined at at temperature of 900° C. Thus 100 of the mica coated on the surface thereof with titanium dioxide (i.e., titanated mica) was obtained.

The titanated mica thus obtained was subjected to a reducing treatment under a gas mixture stream of 1 liter/min of ammonia and 3 liter/min of nitrogen at a temperature of 800° C. for 4 hours. After cooling, 100 g of the powder particles (i.e., intermediate "B") exhibiting green pearl gloss both in the appearance color and the interference color was recovered.

The compositions of the intermediated "B" obtained in the same manner as in Example 1 were 49.5% of mica, 10.1% of titanium dioxide, and 40.4% of titanium oxynitride. This intermediate "B" was represented by $Ti_{0.35}N_{0.29}O_{0.37}$ from the determination of the oxygen and nitrogen contents.

A 50 g amount of the intermediate "B" obtained above was added to 500 g of ion-exchanged water and was uniformly dispersed therein while thoroughly stirring. Then, 212.5 g of a 40% aqueous titanyl sulfate solution was added to the dispersion obtained above. The mixture was boiled upon heating for 6 hours, while stirring. After cooling, the mixture was filtered, washed with water, and dried at a temperature of 200° C. Thus, 84 g of the desired titanium-mica composite material (i.e., the mica coated with the titanium compounds) in the form of powder particles was obtained.

The resultant powder particle had a green appearance color and a consistent interference color and also exhibited pearl gloss. The compositions of the product determined in the same manner as in Example 1 were 29.3% of mica, 46.9% of titanium dioxide, and 23.8% of titanium oxynitride.

EXAMPLE 5

(Preparation)

A 50 g amount of the intermediate "B" obtained in the same manner as in Example 4 was added to 500 g of ion-exchanged water and was uniformly dispersed therein while thoroughly stirring. Then, 156 g of a 40% aqueous titanyl sulfate solution was added to the dispersion obtained above. The mixture was boiled upon heating for 6 hours, while stirring. After cooling, the mixture was filtered, washed with water, and dried at a temperature of 200° C. Thus, 75 g of the desired titanium-mica composite material (i.e., the mica coated with the titanium compounds) in the form of powder particles was obtained.

The resultant powder particle had a bright reddish purple appearance color and a consistent interference color and also exhibited pearl gloss. The compositions of the product determined in the same manner as in Example 1 were 32.8% of mica, 40.4% of titanium dioxide, and 26.8% of titanium oxynitride.

EXAMPLE 6

(Preparation)

A 50 g amount of the intermediate "B" obtained in the same manner as in Example 4 was added to 500 g of ion-exchanged water and was uniformly dispersed therein while thoroughly stirring. Then, 187.5 g of a 40% aqueous titanyl sufate solution was added to the dispersion obtained above. The mixture was boiled upon heating for 6 hours, while stirring. After cooling, the mixture was filtered, washed with water, and dried at a temperature of 200° C. Thus, 80 g of the desired titanium-mica composite material (i.e., the mica coated with the titanium compounds) in the form of powder particles was obtained.

The resultant powder particle had a bright blue appearance color and a consistent inteference color and also exhibited pearl gloss. The compositions of the product determined in the same manner as in Example 1 were 30.7% of mica, 44.2% of titanium dioxide, and 25.1% of titanium oxynitride.

The powder products obtained in the above-mentioned Examples 1 to 6 were evaluated by the following tests.

(1) The appearance color and the interference color were visually observed.

(2) The color tone was determined in terms of hue (H), brightness (V), and chroma in a powder-cell method by means of a color analyzer 607 (manufactured by HITACHI, LTD).

(3) The acid stability was evaluated as follows:

A 1.5 g amount of the sample was charged into a 50 ml test tube with a stopper and 30 ml of a 2N HCl solution was added thereto. Thus, the sample was dispersed in the HCl solution and the test tube allowed to stand in a test tube stand. After 24 hours, the results were visually evaluated in accordance with the following criteria:

++: No color tone change and extremely stable
±: Gradually fade and become pale and whitish
−: Fade and become white (4) The alkali stability was evaluated as follows:

A 1.5 g amount of the sample was charged into a 50 ml test tube provided with a stopper, and 30 ml of a 2N NaOH solution was then added thereto. The resultant dispersion in the test tube was allowed to stand in a test tube stand. After 24 hours, the results were visually evaluated in accordance with the following criteria:

++: No color tone change and extremely stable
±: Gradually fade and become whitish
−: Fade and become white (5) The light stability was evaluated as follows:

A sample was mixed with talc (manufactured by Asada Seifun Co.) in a ratio of 3:7 and 2.5 g of the mixture was molded to the shape of a square having a side length of 20 mm and a thickness of 3 mm in an inner aluminum dish. The molded sample was irradiated by a xenon lamp for 30 hours. The color tones of the sample before the irradiation and after the irradiation were measured by a color analyzer 607 and the color difference ($\Delta E$) before and after the irradiation was calculated from the measured color values.

(6) The heat stability was evaluated as follows:

A 3 g amount each of the sample was weighed in a 20 ml porcelain crucible and was heat treated at a temperature of 200° C., 300° C. and 400° C. for 2 hours in the air. The color of the powder after the treatment was determined by means of a color analyzer 607 and the color difference ($\Delta E$) before and after the heat treatment was calculated. Furthermore, the color change was visually observed when the color change before and after the heat treatment was remarkable.

(7) The dispersion stability was evaluated as follows:

A 1.0 g amount of the sample was charged into a 50 ml graduated test tube provided with a stopper and 50 ml of a 0.2% hexamethaphosphoric acid was then added thereto. The sample was dispersed for 30 seconds in a POLYTRON (manufactured by KINEMATICA) and the dispersion was further dispersed by an ultrasonic wave. After dispersion, the test tube was allowed to stand in a test tube stand. The dispersion conditions were visually observed immediately after standing in the test tube stand and also after 5, 10, 30, and 60 minutes. The results were evaluated in accordance with the following criteria:

+: No sedimentation and good dispersibility
±: Sedimentation is progressing with color segregation
−: Complete sedimentation with color segregation As comparative tests, the following comparative samples 1 to 5 were also evaluated in the above-mentioned test items.

| Comparative pigment sample 1: | Cloisonne' Gemtone Amethyst* |
| Comparative pigment sample 2: | Cloisonne' Gemtone Sapphire* |
| Comparative pigment sample 3: | Cloisonne' Super Green* |
| Comparative pigment sample 4: | Intermediate "A" in Example 1 |
| Comparative pigment sample 5: | Intermediate "B" in Example 4 |

*Commercially available pigments manufactured by Mearl Co., U.S.A.

The test results are shown in Table 2.

TABLE 2

| Sample | (1) Appearance color | (1) Interference color | (2) Tone (H/V/O) | (3) Acid stability | (4) Alkali stability | (5) Light stability | (6) Heat stability 200° C. | (6) Heat stability 300° C. | (6) Heat stability 400° C. | (7) Dispersion stability |
|---|---|---|---|---|---|---|---|---|---|---|
| Example No. | | | | | | | | | | |
| 1 | Green | Same as left | 4.8 G/4.0/3.8 | ++ | ++ | 0.12 | 0.10 | 0.10 | 0.16 | + |
| 2 | Reddish purple | Same as left | 7.5 P/5.0/6.2 | ++ | ++ | 0.10 | 0.10 | 0.12 | 0.15 | + |
| 3 | Blue | Same as left | 10 PB/4.5/7.2 | ++ | ++ | 0.13 | 0.10 | 0.11 | 0.15 | + |
| 4 | Green | Same as left | 5.0 G/3.7/5.2 | ++ | ++ | 0.10 | 0.10 | 0.13 | 0.18 | + |
| 5 | Reddish purple | Same as left | 7.6 P/3.2/4.6 | ++ | ++ | 0.10 | 0.09 | 0.11 | 0.16 | + |
| 6 | Blue | Same as left | 7.5 PB/5.2/7.7 | ++ | ++ | 0.09 | 0.10 | 0.11 | 0.15 | + |
| Comparative Example No. | | | | | | | | | | |
| 1 | Reddish purple | Same as left | 6.25 P/3.2/5.0 | − | − | 21.30 | Decrease in chroma 7.2 | Yellowish red 31.6 | Yellowish white 52.3 | − |
| 2 | Blue | Same as left | 9.0 PB/6.0/8.2 | ± | − | 6.30 | Decrease in chroma 5.6 | Reddish brown 37.2 | Reddish brown 40.0 | − |
| 3 | Green | Same as left | 3.2 G/4.6/3.75 | ± | − | 4.30 | Decrease in chroma 7.8 | Reddish brown 45.1 | Reddish brown 58.3 | − |
| 4 | Blue | Same as left | 9.4 PB/3.18/2.36 | ++ | ++ | 0.20 | 0.11 | 0.13 | 0.25 | + |
| 5 | Green | Same as left | 8.77 B/3.23/2.22 | ++ | ++ | 0.10 | 0.10 | 0.13 | 0.20 | + |

As is clear from the results shown in Table 2, the samples of Examples 1 to 6 according to the present invention have excellent color tone such as brightness and chroma, good consistency between the appearance color and the interference color, and excellent acid resistance, alkali resistance, light resistance, heat resistance, and dispersion stability.

EXAMPLE 7

(Preparation)

A 50 g amount of mica was added to 500 g of ion-exchanged water and was uniformly dispersed therein while thoroughly stirring. Then, 30 g of a 40 % aqueous titanyl sulfate solution was added to the dispersion obtained above. The mixture was boiled upon heating for 3 hours, while stirring. After cooling, the mixture was filtered, washed with water, and dried at a temperature of 100° C. Thus, 54 g of the mica coated on the surface thereof with titanium dioxide (i.e., titanated mica) was obtained.

A 50 g amount of the titanated mica thus obtained was uniformly mixed with 1.7 g of metallic titanium powder in a small-sized mixer. The powder mixture thus obtained was subjected to a thermal treatment at a temperature of 900° C. in vacuo for 6 hours. After cooling, 51 g of the powder particles (i.e., intermediate "C") exhibiting black pearl gloss both in the appearance color and the interference color were recovered.

The compositions of the intermediate "C" thus obtained so determined in the same manner as in Example 1 were 91% of mica and 9%, in terms of TiO, of the low oxides of titanium.

A 50 g amount of the intermediate "C" obtained above was added to 500 g of ion-exchanged water and was uniformly dispersed therein while thoroughly stirring. Then, 10 g of a 40% aqueous titanyl sulfate solution was added to the dispersion obtained above. The mixture was boiled upon heating for 2 hours, while stirring. After cooling, the mixture was filtered, washed with water, and dried at a temperature of 100° C. Thus 51 g of the desired titanium-mica composite material (i.e., the mica coated with the titanium compounds) in the form of powder particles was obtained.

The resultant powder particle had a bright black appearance color and a consistent interference color and also exhibited pearl gloss. The compositions of the product determined in the same manner as in Example 1 were 88.1% of mica, 3.2% of titanium dioxide, and 8.7%, in terms of TiO, of the low oxides of titanium.

The product was evaluated in the same manner as in Examples 1 to 6. The results are shown in Table 3.

EXAMPLE 8

(Preparation)

A 50 g amount of mica was added to 500 g of ion-exchanged water and was uniformly dispersed therein while thoroughly stirring. Then, 312.5 g of a 40% aqueous titanyl sulfate solution was added to the dispersion obtained above. The mixture was boiled upon heating for 3 hours, while stirring. After cooling, the mixture was filtered, washed with water, and dried at a temperature of 200° C. Thus, 100 g of the mica coated on the surface thereof with titanium dioxide (i.e., titanated mica) was obtained.

A 100 g amount of the titanated mica thus obtained was uniformly mixed with 7.5 g of metallic titanium powder in a small-sized mixer. The powder mixture thus obtained was subjected to a thermal treatment at a temperature of 900° C. in vacuo for 6 hours. After cooling, 105 g of the powder particles (i.e., intermediate "D") exhibiting green pearl gloss both in the appearance color and the interference color were recovered.

A 100 g amount of the intermediate "D" obtained above was added to 100 g of ion-exchanged water and was uniformly dispersed therein while thoroughly stirring. Then 425 g of a 40% aqueous titanyl sulfate solution was added to the dispersion obtained above. The mixture was boiled upon heating for 6 hours, while stirring. After cooling, the mixture was filtered, washed with water, and dried at a temperature of 200° C. Thus 168 g of the desired titanium-mica composite material (i.e., the mica coated with the titanium compounds) in the form of powder particles was obtained.

The resultant powder particle had a bright green appearance color and a consistent interference color and also exhibited pearl gloss. The compositions of the product determined in the same manner as in Example 1 were 29.3% of mica, 47.3% of titanium dioxide, and 23.4%, in terms of TiO, of the low oxide of titanium.

The product was evaluated in the same manner as in Examples 1 to 6. The results are shown in Table 3.

EXAMPLE 9

(Preparation)

A 50 g amount of mica was added to 500 g of ion-exchanged water and was uniformly dispersed therein while thoroughly stirring. Then, 200 g of a 40% aqueous titanyl sulfate solution was added to the dispersion obtained above. The mixture was boiled upon heating for 3 hours, while stirring. After cooling, the mixture was filtered, washed with water, and dried at a temperature of 200° C. Thus, 80 g of the mica coated on the surface thereof with titanium dioxide (i.e., titanated mica) was obtained.

A 50 g amount of the titanated mica thus obtained was uniformly mixed with 3 g of metallic titanium powder in a small-sized mixer. The powder mixture thus obtained was subjected to heat treatment at a temperature of 900° C. in vacuo for 6 hours. After cooling, 52 g of the powder particles (i.e., intermediate "E") exhibiting reddish purple pearl gloss both in the appearance color and the interference color was recovered.

A 50 g amount of the intermediate "E" obtained above was added to 500 g of deionized water and was uniformly dispersed therein while thoroughly stirring. Then, 50 g of a 40% aqueous titanyl sulfate solution was added to the dispersion obtained above. The mixture was boiled upon heating for 6 hours, while stirring. After cooling, the mixture was filtered, washed with water, and dried at a temperature of 200° C. Thus, 57 g of the desired titanium-mica composite material (i.e., the mica coated with the titanium compounds) in the form of powder particles was obtained.

The resultant powder particle had a bright blue appearance color and a consistent interference color and also exhibited pearl gloss. The compositions of the product determined in the same manner as in Example 1 were 49.3% of mica, 34.4% of titanium dioxide, and 16.3%, in terms of TiO, of the low oxide of titanium.

The product was evaluated in the same manner as in Examples 1 to 6. The results are shown in Table 3.

TABLE 3

| Example No. | 7 | 8 | 9 |
|---|---|---|---|
| Appearance color | Black | Green | Blue |
| Interference color | " | " | " |
| Color tone H/V/C | | 7.7 G/6.0/9.8 | 9.6 B/5.0/9.5 |
| Acid stability | ++ | ++ | ++ |
| Alkali stability | ++ | ++ | ++ |
| Light stability | | 0.11 | 0.09 |
| Heat stability | | | |
| 200° C. | | 0.09 | 0.09 |
| 300° C. | | 0.11 | 0.10 |
| 400° C. | | 0.15 | 0.13 |
| Dispersion stability | + | + | + |

As is clear from the results shown in Table 3, the samples of Examples 7 to 9 according to the present invention have excellent color tone such as brightness and chroma, good consistency between the appearance color and the interference color, and excellent acid resistance, alkali resistance, light resistance, heat resistance, and dispersion stability.

EXAMPLE 10

(Application)

A pressed powder type eye shadow having the following composition was prepared.

| Ingredient | Part |
| --- | --- |
| Kaolin | 20.0 |
| Mica | 21.5 |
| Product of Example 3 | 50.0 |
| Glyceryl tri 2-ethylhexanoate | 2.0 |
| Squalane | 5.0 |
| Glyceryl monostearate | 0.5 |
| Preservative | q.s. |
| Perfume | q.s. |

The kaolin and the mica were first mixed together. After the mixture was grounded, the powder mixture was mixed with the product of Example 3. The other ingredients previously mixed and melted were added to the resultant mixture and thoroughly mixed together. The mixture thus obtained was molded to prepare the desired solid powder type eye shadow.

COMPARATIVE EXAMPLE 1

(Application)

A pressed powder type eye shadow was prepared in the same manner as in Example 10, except that the product of Example 3 used in Example 10 was replaced with a conventional blue titanated mica pigment.

The eye shadows prepared in Example 10 and Comparative Example 1 were evaluated as follows.

The sample eye shadow were allowed to stand for 14 days in a constant temperature bath at a temperature of 50° C. The eye shadow was then subjected to an organoleptic odor test. As a result, no foreign odor was generated in the eye shadow of Example 10, but foreign odor was found to be generated in the eye shadow of Comparative Example 1, probably due to the activity of ferro ferricyanide present in the commercially available blue pigment. Furthermore, 3.0 g of the eye shadow was charged into a 50 ml test tube provided with a stopper, and ml of a 0.1N NaOH solution was then added to the test tube. Thus, the eye shadow was dispersed in the alkali solution. The test tube was allowed to stand for 24 hours in a test tube stand. After 24 hours, the conditions of the eye shadow in the test tube were observed. As a result, the eye shadow of Example 10 was not decolored and was stable, whereas that of Comparative Example 1 was discolored to yellowish red.

EXAMPLE 11

(Application) A stick type eye shadow having the following composition was prepared.

| Ingredient | Part |
| --- | --- |
| Ultramarine blue (purple) | 12.0 |
| Talc | 10.0 |
| Titanium dioxide | 2.0 |
| Product of Example 5 | 20.0 |
| Carnauba wax | 2.0 |
| Beeswax | 4.0 |
| Solid paraffin | 10.0 |
| Squalane | 21.0 |
| Glyceryl tri 2-ethylhexanoate | 19.0 |
| Sorbitan sesquioleate | 1.0 |
| Preservative | q.s. |
| Perfume | q.s. |

A portion of the squalane and the sorbitan sesquioleate were added to the ultramarine blue, talc, titanium dioxide, and the product of Example 5 and the mixture was subjected to a colloid mill treatment. Thus, the pigment part was prepared.

The other ingredients were mixed and dissolved upon heating. The pigment part obtained above was added to the molten mixture, and the mixture was uniformly dispersed in a homomixer. After dispersing, the dispersion was cast in a mold, followed by quenching. Thus, the desired stick type eye shadow was obtained.

The eye shadow thus obtained was stable without causing any foreign odor generation and discoloration as the eye shadow in Example 10.

EXAMPLE 12

(Application)

A nail enamel having the following composition was prepared.

| Ingredient | Part |
| --- | --- |
| Nitrocellulose | 10.0 |
| Alkyd resin | 10.0 |
| Acetyltributyl citrate | 5.0 |
| Ethyl acetate | 20.0 |
| Butyl acetate | 15.0 |
| Ethyl alcohol | 5.0 |
| Toluene | 34.0 |
| Lithol rubine BCA | 0.5 |
| Product of Example 2 | 0.4 |
| Iron oxide (red) | 0.1 |
| Suspension stabilizer | q.s. |

The lithol rubine BCA and ultramarine blue were added to a portion of the alkyd resin and a portion of the acetyltributyl citrate and the mixture was thoroughly incorporated. Thus, the pigment part was prepared.

The remaining ingredients except for the product of Example 2 were mixed and dissolved. In the resultant solution, the pigment part obtained above and the product of Example 2 were uniformly dispersed to obtain the desired nail enamel.

COMPARATIVE EXAMPLE 2

(Application)

A nail enamel was prepared in the same manner as in Example 12, except that the product of Example 2 was replaced with a commercially available conventional blue titanated mica pigment.

The sample nail enamels of Example 12 and Comparative Example 2 were evaluated as follows.

A 10 ml amount of the nail enamel was charged into a 20 ml glass vessel with a stopper and was then irradiated by a xenon lamp for 30 hours. The sample was then coated on a hiding power test paper (manufactured by NIPPON TEST PANEL KOGYO) at a thickness of 0.45 mm to compare the color tone before and after the irradiation. The color tone was determined by means of a color analyzer 607 and the color difference ($\Delta E$) before and after the irradiation was calculated from the results of the determination.

As a result, $\Delta E$ of the nail enamel of Example 12 was 0.1, which was stable without causing any discoloration. Contrary to this, $\Delta E$ of the nail enamel of Comparative Example 2 was 1.8, which caused discoloration.

EXAMPLE 13

(Application)

A lipstick having the following composition was prepared as follows.

| Ingredient | Part |
| --- | --- |
| Titanium dioxide | 4.5 |
| Iron oxide (red) | 0.5 |
| Yellow #4 aluminum lake | 0.6 |
| Red #223 | 0.2 |
| Product of Example 5 | 1.0 |
| Candelilla wax | 9.0 |
| Solid paraffin | 8.0 |
| Beeswax | 5.0 |
| Carnauba wax | 5.0 |
| Lanolin | 10.0 |
| Castor oil | 40.8 |
| Isopropyl myristate | 15.0 |
| Perfume | q.s. |
| Antioxidant | q.s. |

The titanium dioxide, iron oxide (red), and yellow #4 aluminum lake were added to a portion of the castor oil and the mixture was treated on rollers. Thus, the pigment part was prepared. The red #223 was dissolved in a portion of the castor oil. Thus, the dye portion was prepared.

The remaining ingredients other than the product of Example 5 were mixed and melted upon heating. Then, the product of Example 5 as well as the above-prepared pigment part and dye part were added to the molten mixture and the mixture was thoroughly dispersed in a homomixer. After dispersing, the resultant dispersion was casted into a mold, followed by quenching to form a stick type product. The stick was then inserted into a lipstick vessel and the framing was carried out. Thus, the desired lipstick was prepared.

EXAMPLE 14

(Application)

An eye liner having the following composition was prepared as follows:

| Ingredient | Part |
| --- | --- |
| Ion oxide (black) | 0.5 |
| Product of Example 6 | 18.5 |
| Vinyl acetate resin emulsion (40%) | 40.0 |
| Carboxymethyl cellulose (10% aqueous solution) | 15.0 |
| Glycerol | 6.0 |
| Deionized water | 18.0 |
| Polyoxyethylene (20 mole) sorbitan monooleate | 1.0 |
| Preservative | q.s. |
| Perfume | q.s. |

The glycerol and the polyoxyethylene monooleate were added to the ion-exchanged water and were dissolved therein upon heating. The iron oxide (black) was then added to the mixture. The resultant mixture was subjected to a colloid mill treatment. Thus, the pigment part was prepared. The remaining ingredients except for the product of Example 6 were mixed together and the mixture was heated to a temperature of 70° C. To this mixture, the pigment part obtained above and the product of Example 6 were added. The resultant mixture was uniformly dispersed in a homomixer. Thus, the desired eye liner was prepared.

The eye liner thus obtained was very stable without causing any foreign odor generation and also causing any decoloration in an alkali solution.

EXAMPLE 15

(Application)

An eye liner was prepared in the same manner as in Example 14, except that the product of Example 6 used in Example 14 was replaced with the black product of Example 7.

This eye liner was also very stable with good dispersibility and without causing any foreign odor generation.

COMPARATIVE EXAMPLE 3

(Application)

An eye liner was prepared in the same manner as in Example 15, except that the product of Example 7 was replaced with a commercially available conventional black titanated mica pigment (Timica Nu-Antique Silver Mearl Co.).

The eye liners of Example 15 and Comparative Example 3 were evaluated as follows.

The eye liner was allowed to stand for one week in a 20 ml glass vessel with a stopper. As a result, the separation of the black powder was observed in the eye liner of Comparative Example 3. The color difference ($\Delta E$) of the eye liner before and after leaving to stand was determined in the same manner as in Example 12 and Comparative Example 2. The $\Delta E$ of the eye liner of Example 15 was 0.1 (i.e., stable without discoloration). Contrary to this, $\Delta E$ of the eye liner of Comparative Example 3 was 1.0 (i.e., discoloration).

EXAMPLE 16

(Application)

A solid type rouge having the following composition was prepared as follows.

| Ingredient | Part |
| --- | --- |
| Iron oxide (red) | 0.2 |
| Red #226 | 0.5 |
| Product of Example 2 | 5.0 |
| Mica | 54.3 |
| Talc | 24 |
| Glyceryl tri 2-ethylhexanoate | 5.0 |
| Vaseline | 2.0 |
| Squalane | 6.0 |
| Sorbitan sesquioleate | 1.5 |
| Perfume | q.s. |
| Preservative | q.s. |

The iron oxide (red), red #226, mica, and talc were thoroughly mixed together in a kneader. Thus, the pigment part was prepared. The aqueous phase (i.e., the purified water) was kept at a temperature of 70° C. The oil was prepared by mixing the remaining ingredient other than the perfume and the product of Example 2 and the mixture was dissolved upon heating at a temperature of 70° C.

The oil phase having a temperature of 70° C. was added to the aqueous phase having a temperature of 70° C. The mixture was uniformly emulsified in a homomixer. The emulsion was added to the powder part. The mixture was kneaded in a kneader, followed by vaporizing the water. The resultant mixture was treated in a grinder. While the powder mixture obtained above was stirred, the perfume was uniformly sprayed thereover and the product (i.e., mica coated with the specified titanium compounds) of Example 2 was uniformly mixed with the powder mixture. The mixture was compression molded to form the desired solid type rouge.

COMPARATIVE EXAMPLE 4

(Application)

A solid type rouge was prepared in the same manner as in Example 16, except that the product of Example 2 used in Example 16 was replaced with a commercially available conventional reddish purple titanated mica pigment.

The rouges of Example 16 and Comparative Example 4 were evaluated as follows.

A 5 g amount of the sample rouge was charged into a 20 ml glass vessel with a stopper and was irradiated for 30 hours by means of a xenon lamp. The color difference ($\Delta E$) before and after the irradiation was determined in the same manner as in Example 12 and Comparative Example 2. As a result, $\Delta E$ of the rouge of Example 16 was 0.1 (i.e., stable without discoloration), whereas that of Comparative Example 3 was 1.3 (i.e., discolored to brown).

Furthermore, the difference in the color tint between the appearance color of the product and the applied color of the coating of the rouges of Example 16 and Comparative Example 4 were organoleptically evaluated by a panel consisting of 30 Japanese females having an age of 18 to 24.

The results are shown in Table 4.

TABLE 4

|  | Light-skin Japanese females (10) | Ordinary-skin Japanese females (10) | Dark-skin Japanese females (10) |
| --- | --- | --- | --- |
| Rouge of Example 16 |  |  |  |
| Consistency of appearance color and applied color | 9/10 | 10/10 | 8/10 |
| Inconsistency of appearance color and applied color | 1/10 | 0/10 | 2/10 |
| Rouge of Comparative Example 4 |  |  |  |
| Consistency of appearance color and applied color | 7/10 | 8/10 | 6/10 |
| Inconsistency of appearance color and applied color | 3/10 | 2/10 | 4/10 |

As is clear from the above results, 90% of the panelists recognized consistency of the appearance color and the applied color in the case of the rouge of Example 16, whereas 30% of the panelists had an opinion that the applied color of the rouge of Comparative Example 4 partially caused color segregation or uneven color and exhibited more reddish applied color compared with the appearance color.

We claim:

1. A titanium-mica composite material produced by first coating mica with titanium dioxide, heating the coated mica in the presence of a reducing gas to at least partially convert the titanium dioxide first coat to the low oxides of titanium or to a titanium oxynitride, and applying thereto a second coating of titanium dioxide.

2. A titanium-mica composite material as claimed in claim 1, wehrein the amount of the low oxides and/or the titanium oxynitride in the first coating is 0.01 to 60 parts by weight, based on 100 parts by weight of the mica.

3. A titanium-mica composite material as claimed in claim 1, wherein the thickness of the first coating is 200 Å or more.

4. A titanium-mica composite material as claimed in claim 1, wherein the thickness of the second coating is 50 Å to 5000 Å.

5. A process for producing a composite material comprising coating mica with titanium dioxide, followed by heating in the presence of a reducing gas, to at least partially convert the coated titanium dioxide to the low oxides of titanium or the titanium oxynitrides and then by forming the second coating composed of titanium dioxide.

6. A process according to claim 5, wherein the low oxides of titanium are formed by reducing the coated titanium dioxide with hydrogen.

7. A process according to claim 5, wherein the low oxides of titanium are formed by heating, in vacuo, a mixture of the coated titanium dioxide with metallic titanium.

8. A process according to claim 5, wherein the titanium oxynitrides are formed by reducing the coated titanium dioxide with ammonia.

9. A process according to claim 5, wherein the second coating is produced by heating the low oxides of titanium in such a manner that the outside portion of the coating of the low oxides of titanium is oxidized to form the second coating.

10. A process according to claim 5, wherein the second coating is produced by hydrolizing an inorganic salt of titanium in the presence of the mica coated with the first coating to deposit a hydrous titanium oxide coating on the first coating, followed by heating.

11. A process according to claim 5, wherein the mica coated with the first coating is mixed with metallic titanium, followed by heating.

12. A coloring composition comprising a base and a coloring agent which is a titanium-mica composite material according to claim 1.

13. A cosmetic composition comprising a cosmetic base and a coloring agent which is a titanium-mica composite material according to claim 1.

* * * * *